US006645485B2

(12) United States Patent
Dunn

(10) Patent No.: US 6,645,485 B2
(45) Date of Patent: Nov. 11, 2003

(54) METHOD OF TREATING INFLAMMATION IN THE JOINTS OF A BODY

(76) Inventor: Allan R. Dunn, 1790 Sans Souci Blvd., North Miami, FL (US) 33181

( * ) Notice: Subject to any disclaimer, the term of this patent is extended or adjusted under 35 U.S.C. 154(b) by 0 days.

(21) Appl. No.: 09/778,397

(22) Filed: Feb. 2, 2001

(65) Prior Publication Data

US 2002/0107188 A1 Aug. 8, 2002

Related U.S. Application Data

(60) Provisional application No. 60/214,592, filed on Jun. 27, 2000, and provisional application No. 60/202,561, filed on May 10, 2000.

(51) Int. Cl.$^7$ .......................... A61K 38/18; A61K 45/00
(52) U.S. Cl. ........................ 424/85.1; 424/426; 514/12; 514/886; 530/840
(58) Field of Search ................................ 424/85.1, 426; 514/12, 886; 530/840

(56) References Cited

U.S. PATENT DOCUMENTS 5,368,051 A * 11/1994 Dunn et al. .................. 128/898

* cited by examiner

*Primary Examiner*—Gary Kunz
*Assistant Examiner*—Fozia Hamud
(74) *Attorney, Agent, or Firm*—Malloy & Malloy, P.A.

(57) ABSTRACT

A process for treating inflammation in a joint whether heat, redness, pain, swelling and/or stiffness, and for increasing motion and increasing joint space and correcting malalignment, comprising the steps of dissolving a quantity of growth hormone (somatotropin), preferably in purified form, in a buffer solution, and injecting one time or multiple repeat times, a single dosage of the mixture of purified growth hormone and buffer solution into the joint of a body so as to initiate the treatment process.

20 Claims, 1 Drawing Sheet

METHOD OF TREATING INFLAMMATION IN THE JOINTS OF A BODY

CLAIM OF PRIORITY

This application claims priority to the U.S. provisional patent applications having Ser. Nos. 60/202,561 and 60/214,592 filed on May 10, 2000 and Jun. 27, 2000, respectively, both of which are incorporated herein by reference.

BACKGROUND OF THE INVENTION

1. Field of the Invention

The present invention relates to a process of treating inflammation in a joint, such as but not limited to a knee joint, a hip joint or an ankle joint, which has been damaged or which has otherwise become defective, and thereby, alleviating pain, heat, redness, swelling, stiffness, and other difficulties typically associated with a damaged or defective articular cartilage surface in a joint. More in particular, the present invention is directed to a process of injecting a mixture of purified growth hormone (commonly known as somatotropin) and a buffer solution into the joint of a body, preferably but not limited to that of a human, so as to initiate the treatment process.

2. Description of the Related Art

The ends of bones which form a joint, including vertebra, are covered by articular cartilage, which is a thin, fragile tissue layer and which allows the bone ends to move freely and without pain. Many arthritic diseases and many degrees of trauma can, however, cause destruction or deterioration of this fragile layer. From ancient times and continuing in the present day, people have suffered through varying degrees of heat, redness, pain, swelling and/or stiffness of the joints, any one or all of which can often be associated with deterioration of the articular cartilage in the joints, whether those joints are associated with walking, such as the hip, knee or ankle joints or others, such as the vertebra of the spine, the shoulder, elbow or wrist joints and fingers. Regardless, damage to and/or the deterioration of articular cartilage in a joint is often, if not always accompanied by inflammation. Inflammation, which is typically thought of as heat, redness, pain, swelling and/or stiffness, when experienced in a joint, can be crippling.

As a result, many have tried to develop ways to alleviate the pain and inflammation associated with arthritis and other damage to the joints. A number of these efforts have focused on oral medications such as cortisone derivatives (steroids) and numerous non-steroidal anti-inflammatory drugs (NSAIDs), all of which have potentially serious side effects. Other efforts have focused on implants of entire joints, such as the knee or hip, although typically, a lengthy and complicated surgical procedure is required, with the patient being forced to undergo a significant recovery period, including a rigorous and costly regimen of physical therapy thereafter. Most often, full motion and full activity are not achieved with the use of these implants. While medical science has recently developed a variety of new materials for the joint implants, these implants are often more costly, offer results which may be only marginally better than those obtained previously, and do nothing to avoid the hospitalization required for the surgical implantation of them nor the long periods of rehabilitation. In addition, it is also possible that one or more revision surgeries will be needed to replace defective, loose or infected implants. Further, the general discomfort which might be associated with utilizing such implants makes an alternative method all the more desirable.

The biological action of growth hormone, namely, somatotropin, has been the subject of the inventor's research. Heretofore, growth hormone has been used clinically to enhance the growth of children with short stature. Somatotropin may have other effects on other organ systems but in the instant application for a patent, the specific actions of somatotropin related to its effects on articular cartilage have been focused on by Dunn's research and are utilized herein. The major targets of somatotropin activity are believed by the inventor hereof to be vascular sinusoids and sub-chondral vessels located at the cartilage-bone interface (sub-chondral bone) and the endothelial cells located therein, and in addition, nests of stem (pleuripotential) cells in various sites such as marrow; and the vascular system. More specifically, it is believed by the inventor hereof that growth hormone has the ability to stimulate proliferation of stem cells in the marrow and subchondral vessels and sinusoids. The inventor hereof has also shown that growth hormone has the ability to form vascular and multi-lumen sinusoids, known as Glomeruloids, from pre-existing and mature single lumen vessels in the sub-chondral bone. The inventor describes this action of growth hormone as Morphogenic Action, which is a type of rejuvenation of mature monolumen vessels into fetal-like and/or other immature chondrogenic vascular structures. This Morphogenic Action, a type of rejuvenation, can also dematurate a layer of mature sub-chondral bone into a cartilaginous state comparable to that observed in the neonatal and immature cartilaginous skeleton.

The method of this invention relies on a novel use of growth hormone, namely, somatotropin. More in particular, the method of the present invention is useful as an anti-inflammatory agent and is specifically adapted to treat inflammation (heat, redness, pain, swelling, stiffness, etc.) and/or pain associated with damaged and/or defective articular cartilage on or at a joint in a body through the injection directly into the joint of one or more dosages of purified growth hormone (somatotropin). There is no reliance on the transplantation of tissue and thus all of the detrimental conditions of rejection, immune reaction, and other causes of transplant failure are avoided. Similarly, the present invention does not require an individual to undergo a lengthy or complicated surgical procedure, such as those which accompany joint replacements.

Until the present invention, growth hormone has not, to the inventor's knowledge, ever been used to treat merely the inflammation of tissues such as the soft tissue components within and surrounding a joint, i.e., synovial lining, capsule, and ligaments and articular cartilage and/or the pain associated therewith. Of course, the inventor herein has heretofore focused on growth hormone as a means for regenerating articular cartilage in a joint, for which U.S. Pat. No. 5,368,051 was awarded, incorporated herein by reference, but he has since improved and refined the applications for which growth hormone may be used, as set forth in greater detail, below.

Accordingly, the method of the present invention provides a much needed improvement in the treatment and elimination of ailments associated with the deterioration or destruction of the articular cartilage surface of a joint, including pain, inflammation of the soft tissue components within and surrounding the joint, including heat, redness, pain, swelling or stiffness. The method of the present invention also is directed towards providing for the reappearance or increase of space between bone ends and restoration of normal alignment of a limb, such as a leg, and including the restoration of normal or nearly normal motion.

SUMMARY OF THE INVENTION

The present invention is directed towards a method of treating inflammation and pain in a joint separating two or more bones. It is pointed out that for purposes of this application, inflammation means pain, joint stiffness, redness, heat and/or swelling, etc.

The method comprises an initial step of dissolving a quantity of growth hormone in a buffer solution and then injecting the resulting mixture as a single loading dose into the joint cavity where it will lessen the inflammation of the synovial lining, joint capsule, ligaments and articular cartilage. If desired or needed, additional injections of growth hormone of a single dosage can be injected from one day to several weeks later and after a first set of single or multiple injections, several additional sets of single or multiple injections may be given so as to maintain any improvement of the function of the joint.

In one alternative embodiment, the method of the present invention may comprise an additional step of mixing an amount of Lidocaine, anywhere from about 0.5 milliliter to 10 milliliters, and ideally about 1 to 3 milliliters of Lidocaine with the mixture of growth hormone and buffer solution. It is contemplated that other injectable anesthetics aside from Lidocaine might also be used with the present invention.

It is a primary object of the present invention to provide a method for reducing the inflammation of tissue located in or at the joints of a body as well as pain arising at or within the joint of a body without requiring a surgical procedure.

It is also a primary object of the present invention to provide a new treatment for pain and inflammation in the joint of a body which relies upon a lower dosage of growth hormone and an alternative buffer solution other than that described previously in the applicant's U.S. Pat. No. 5,368,051 directed to regenerating articular cartilage.

A feature thought to arise following treatment of a joint with the present invention is that contact or near contact between the bone-to-bone surfaces is reversed, meaning that a separation, distance or space between the bony surfaces is restored, presumably but perhaps not exclusively because the treatment causes some resumption of growth of articular cartilage, such as that which has been worn down.

An advantage of the present invention over that disclosed in the Applicant's previous patent is that a range of motion is restored to a joint following treatment.

Another advantage of the present inventive treatment is the smoothing of irregular joint surfaces and sub-chondral bone and also a reversal of malalignment of the limb following treatment. The present invention thereby eliminates or substantially alleviates ailments in the joints.

These and other objects, features and advantages of the present invention will become more clear when the drawings as well as the detailed description are taken into consideration.

BRIEF DESCRIPTION OF THE DRAWINGS

For a fuller understanding of the nature of the present invention, reference should be made to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
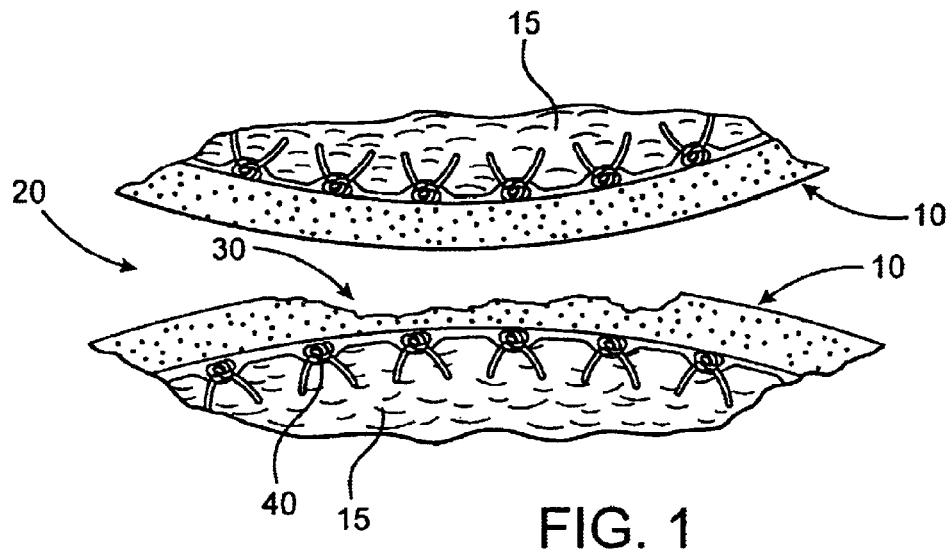
FIG. 1 is a cross-sectional view of a joint surface illustrating a deteriorated articular cartilage on the lower joint surface.

The present invention is directed specifically towards a method of treating inflammation and associated pain in a joint, such as one having damaged or defective articular cartilage 10. Articular cartilage 10, which is present between bones 15 at a joint 20, provides a bearing type surface for facilitated movement between the bones 15 (see FIG. 1). If articular cartilage is damaged or deteriorated, as represented by reference numeral 30 in the drawings, this can result in a person's experiencing significant heat, redness, pain, swelling, stiffness and/or malalignment of the limb or joint, and can even be crippling to some individuals, such as those suffering from a trauma or other ailments which destroy the joint surface. The articular cartilage 10 is a resilient layer of tissue which covers the ends of bones 15, and it has been traditionally assumed that once gone, it cannot be regrown or regenerated, at least until the work by the inventor hereof, some of which has been set forth in U.S. Pat. No. 5,368,051.

The method of the present invention is a significant improvement over what is known in the art for treating the sometimes excruciating pain which individuals experience in one or more of the joints of their bodies. For example, the present invention does not involve a surgical procedure, which would require some recovery therefrom, nor any type of transplantation of tissue. The method of the present invention, which is believed to offer swift relief to the heat, redness, pain, swelling, stiffness or other inflammatory symptoms experienced by individuals suffering from damaged articular cartilage in a joint, offers an improvement over the method described in the inventor's previous U.S. Pat. No. 5,368,051 by relying upon the utilization of a lower dosage of growth hormone and of an alternative buffer solution, and if desired, the addition of injectable anesthetics. The method of the present invention is thought to be effective as a result of the discovery that in addition to the metaphyseal growth plate which exists near the ends of bones and which makes the bones grow during the immature and adolescent periods, there is also an articular growth plate at the joint surface. The metaphyseal growth plate, once achieving full growth within the bone, ceases to function in an adult and disappears. The articular growth plate, however, remains intact, although growth-inactive, at the joint surface in the adult. When properly stimulated by injecting purified growth hormones in the joint, including an anesthetic if desired, as in the method(s) of the present invention, there would be no need for surgically exposing the joint nor for debriding it; the pain and inflammation associated with the damaged articular cartilage is relieved, and this is thought to be because the articular growth plate is stimulated so as to resume active growth.

With reference now to FIG. 1, when an articular cartilage defect as at 30 is present in the joint of an individual, whether a hip joint, knee joint, ankle joint or other type of joint, such that it causes him or her sufficient pain to seek out medical treatment, it is preferable that the individual be required to undergo certain tests in an effort to determine whether treatment in accordance with the present invention is advisable. For example, it is preferred that the individual undergo a complete physical examination by a licensed physician, including any X-rays, MRIs, and/or other laboratory work that may be recommended to hopefully rule out the presence of serious, acute or chronic illnesses and/or whether the individual has a pre-existing excess amount of growth hormone. That is because it is preferred that such persons would not be treated in accordance with the present invention.

Turning more specifically to the method of the present invention, it is directed preferably for use on humans; however, it can be similarly effective with other animals so long as the necessary growth hormone, preferably purified growth hormone, is utilized. It is preferred that the growth hormone be species specific which means that human growth hormone would be used on humans; cattle (bovine) growth hormone would be used on cattle; and horse growth hormone would be used on horses, etc. More in particular, it is preferred that the growth hormone (known as somatotropin) utilized be identical to naturally produced growth hormones of that species. If a biologically engineered hormone alternative were to be used, it should have an amino acid sequence identical to the natural hormone. In the most preferred embodiments, the growth hormone is biologically engineered to exactly duplicate the natural hormone and to assure maximum purity, and avoid the possibility of transmitting disease. For example, if the growth hormone is to be prepared from pituitary glands retrieved from cadavers, the hormone preparation may transmit rare forms of neurological disease even though it may be highly purified.

More in particular, the method of the present invention generally comprises the steps of dissolving a quantity of growth hormone, preferably somatotropin that has ideally been biologically engineered so as to be in a purified state, in a buffer solution and then injecting the resulting solution into the joint having damage which causes an individual to experience pain or inflammation. The quantity of growth hormone to be dissolved in the buffer solution is discussed in greater detail below. The purified growth hormone is typically in the form of a powder and as such, may be readily dissolved in a buffer solution. Preferably, the buffer solution has a range of pH between 5.5 and 8.3, although more preferably, the range of pH is between 6.0 and 8.0. Generally, buffer solutions include a saline solution and have a pH range of approximately 7.0 to 7.4 which is the range of biological pH. In a preferred embodiment, the buffer solution comprises a phosphate buffer which may also include a preservative. In an alternative embodiment, the buffer solution is Hank's Buffer Solution having a higher pH range of about 8.0. Other preparations of purified growth hormone may, due to their chemical composition, require buffer solutions of other ranges of pH.

The growth hormone to be dissolved in the buffer solution can be in a range of between 0.5 milligrams and 10.0 milligrams of growth hormone per milliliter of buffer solution, although a most preferred dosage of about 5.0 to 7.0 milligrams growth hormone, and ideally, 5.8 milligrams of growth hormone per milliliter of buffer solution would be used. This dosage is thought to be operative in accordance with the present inventive method for most human individuals. An alternative dosage to be administered can be more closely related to the person's and/or animal's weight, and will be in the preferred range of 0.025 milligrams to 0.249 milligrams per Kilogram of body weight.

Figure 2:
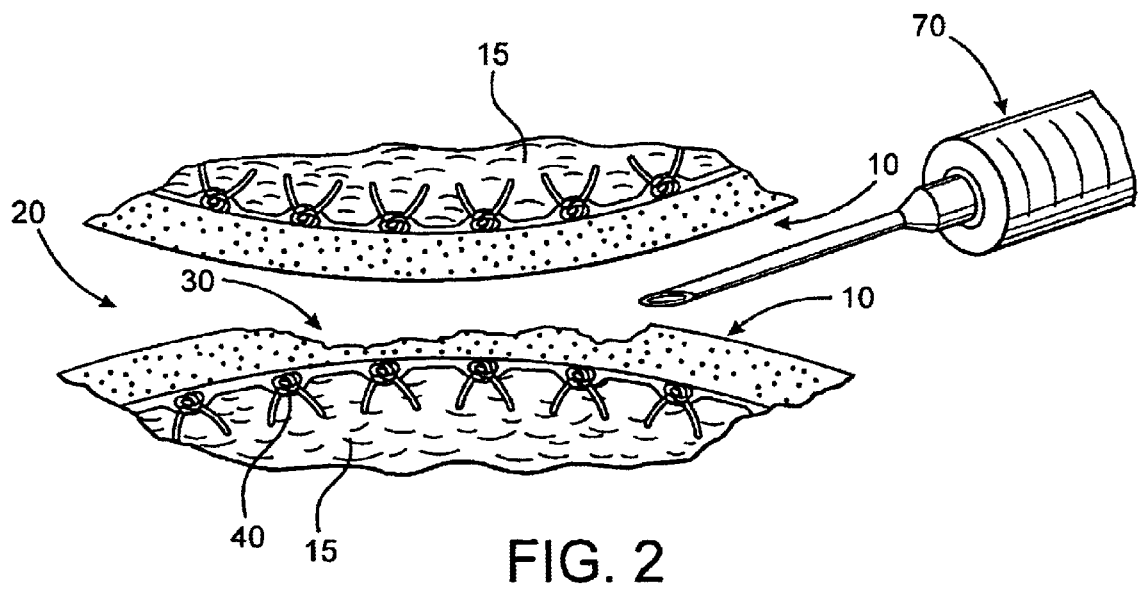
FIG. 2 is an isolated view illustrating the injection of a growth hormone and buffer solution in the joint cavity.

Once the growth hormone and buffer solution have been mixed, a single dosage of the mixture is injected to the joint, as illustrated in FIG. 2. The growth hormone is injected, such as by utilizing a syringe 70, into the joint space and not directly into the bone 15 or tissue. In this manner, it may flow over the entire joint surface and react initially with the tissues on the surface and then with all the vascular units 40 at the bone-cartilage interface. A portion of the purified growth hormone may be absorbed into the bloodstream after about four hours. One of the systemic effects associated with this absorption into the general circulation will be to stimulate production of stem cells in the marrow, vascular system and other areas outside the joint. The growth hormone will cause a reaction in the subchondral vascular structures so as to promote local production of endothelial derived stem cells and also to attract pleuripotential cells to the sinusoidal layer of the bone, the pleuripotential cells being collected in these vascular structures. The reaction will initiate cell layer growth at the sub-chondral layer, and it is believed will eventually produce enough cartilage to form additional joint surface and lead to there being an increased space between the bones of the joint being treated in accordance with the present invention. Depending on the individual patient's condition, repeated, periodical injections of the growth hormone may be required. For example, another single dosage may be injected into the joint in about four weeks, and repeated in another four weeks. Injections could be given and repeated at other time intervals, however, such as every two weeks. Alternatively, single or multiple injections can be given one day, several days, to several weeks or months apart. Such repeated injections of somatotropin or growth hormone may be necessary in situations where a patient suffers from a disease which will continuously impair or destroy the cartilage surface, or antagonize the action of the growth hormone. It is further contemplated that the injection of growth hormone according to the present invention could include the addition of chemical substances which will block or impede the antagonistic action of proteases, present in certain diseases, that might impair or prevent the beneficial action of the growth hormone within the joint.

In an alternative embodiment, the method of the present invention may comprise an additional step of mixing Lidocaine or another local anesthetic with the mixture of growth hormone and buffer solution prior to injection into the joint. In this embodiment, the amount of Lidocaine or other anesthetic to be mixed with the growth hormone and buffer solution may be anywhere from 0.5 milliliters to 10 milliliters, although preferably, about 1 to 3 milliliters will be used.

From the preceding, it is recognized that the present invention may also be considered to include a beneficial anti-inflammatory composition and/or an analgesic composition, both of which may, of course, be utilized within the previously defined methods. Specifically, the anti-inflammatory and/or analgesic composition may comprise a purified growth hormone of between 0.025 milligrams to 0.249 milligrams per kilo of a patient's body weight dissolved in a buffer solution of approximately between 1 to 10 milliliters, preferably as described with regard to the method of treatment, or a purified growth hormone of approximately between 0.5 milligrams to 10.0 milligrams per milliliter of the buffer solution, also preferably as previously recited. Further, a local anesthetic agent, anti-protease agent and/or anti-enzyme agent may be included therewith. In the case of the local anesthetic, it may preferably include Lidocain in an amount of generally between about 0.5 milliliter to 10 milliliters.

Since many modifications, variations and changes in detail can be made to the described preferred embodiment of the invention, it is intended that all matters in the foregoing description and shown in the accompanying drawings be interpreted as illustrative and not in a limiting sense. As examples, the present invention is also claimed in terms of a method for increasing a patient's range of motion in a joint as well as reducing the mal-alignment of a patient's arthritic joint, the latter of which can be characterized as a bow-legged deformity when the joint involved is the knee. In other words, it is the inventor's belief that the intra-articular injection(s) of growth hormone into joint(s) restores normal alignment of osteo-arthritic and post traumatic arthritic knees, such that a bow leg deformity may disappear and the leg can regain normal alignment, and further, or alternatively, that it can restore normal or nearly normal motion in both extension and flexion in osteo-arthritic and post traumatic arthritic knees or other joints. This increased range of motion can be assisted by therapeutic exercise(s), which normally, without treatment in accordance with the present invention, would be extremely painful. In many cases then, therapeutic exercises can only be carried out following treatment with the present invention in as much as the present invention reduces the pain experienced by the patient so as to permit the exercise(s) to occur at all. As another example, the inventor believes that the method of the present invention can be used to treat and/or increase the joint spaces between the vertebrae of the spine, as well. Thus, the scope of the invention should be determined by the appended claims and their legal equivalents.

Now that the invention has been described,

What is claimed is:

1. A method of treating inflammation in a joint of an individual comprising the steps of:
   a) dissolving a range of 0.5 to 10.0 milligrams of purified growth hormone in 1.0 to 10.0 milliliters of a buffer solution, and
   b) injecting a single dosage of said growth hormone and said buffer solution into said joint along the joint surface.

2. A method of treating inflammation as recited in claim 1 wherein said buffer solution has a range of pH between 5.5 and 8.3.

3. A method of treating inflammation as recited in claim 2 wherein said buffer solution is a phosphate buffer solution.

4. A method of treating inflammation as recited in claim 2 wherein said buffer solution is Hank's Buffer Solution having a pH of about 8.0 to 8.3.

5. A method of treating inflammation as recited in claim 2 wherein said growth hormone is species specific so as to be identical to naturally produced growth hormones.

6. A method of treating inflammation as recited in claim 2 wherein said growth hormone is biologically engineered.

7. A method of treating inflammation as recited in claim 6 wherein said single dosage is between 0.025 to 0.249 milligrams of purified growth hormone per Kilogram of body weight.

8. A method of treating inflammation as recited in claim 6 wherein about 5.8 milligrams of said purified growth hormone is dissolved in 1 to 10 milliliters of said buffer solution.

9. A method of treating inflammation as recited in claim 8 further comprising the step of injecting a second one of said single dosage into the joint one week later.

10. A method of treating inflammation as recited in claim 9 further comprising the steps of injecting a third one of said single dosage into the joint one week later.

11. A method of treating inflammation as recited in claim 8 further comprising the steps of injecting a second one of said single dosage into the joint two weeks later.

12. A method of treating inflammation as recited in claim 11 further comprising the steps of injecting a third one of said single dosage into the joint two weeks later.

13. A method of treating inflammation as recited in claim 8 further comprising the step of injecting a second one of said single dosage into the joint four weeks later.

14. A method of treating inflammation as recited in claim 13 further comprising the steps of injecting a third one of said single dosage into the joint four weeks later.

15. A method of treating inflammation as recited in claim 1 further comprising the step of mixing from 0.5 milliliters to 10 milliliters of a local anesthetic with said mixture of growth hormone and buffer solution.

16. A method of treating inflammation as recited in claim 15 wherein the local anesthetic is Lidocaine.

17. A method of treating inflammation as recited in claim 1 further comprising the step of mixing between about 0.5 milliliter to 10 milliliters of Lidocaine with said mixture of growth hormone and buffer solution.

18. A method of treating inflammation as recited in claim 8 further comprising the step of injecting a second one of said single dosage into the joint between one day and four weeks later.

19. A method of treating inflammation in a joint of an individual comprising the steps of:
   a) dissolving a quantity of purified growth hormone in a buffer solution, and
   b) injecting a single dosage of said growth hormone and said buffer solution into said joint along the joint surface, wherein said single dosage comprises between 0–025 and 0.249 milligrams of purified growth hormone per Kilogram of body weight.

20. A method of increasing a patient's range of motion of a joint comprising the injection of at least a single dosage of a growth hormone in a range of 0.025 milligrams to 0.249 milligrams per kilogram of patient body weight dissolved in a buffer solution.

* * * * *